United States Patent
Campion et al.

Patent Number: 5,910,609
Date of Patent: *Jun. 8, 1999

[54] COMPOUNDS

[75] Inventors: Colin Campion; Alan Hornsby Davidson, both of Oxon; Jonathan Philip Dickens, Buckinghamshire; Michael John Crimmin, Ascot, all of United Kingdom

[73] Assignee: British Biotech Pharmaceuticals Limited, Oxford, United Kingdom

[*] Notice: This patent is subject to a terminal disclaimer.

[21] Appl. No.: 08/417,095

[22] Filed: Apr. 5, 1995

Related U.S. Application Data

[62] Division of application No. 07/820,664, filed as application No. PCT/GB90/01117, Jan. 16, 1992.

[30] Foreign Application Priority Data

Aug. 24, 1989 [GB] United Kingdom ................. 8919251

[51] Int. Cl.⁶ ........................... C07D 53/02; C07D 53/04
[52] U.S. Cl. ...................... 562/621; 562/622; 562/623; 564/153
[58] Field of Search .............................. 514/575, 533, 514/547; 562/621, 623, 622; 564/153

[56] References Cited

U.S. PATENT DOCUMENTS

| | | | |
|---|---|---|---|
| 4,105,789 | 8/1978 | Ondetti et al. | 424/309 |
| 4,496,540 | 1/1985 | Kim | 424/320 |
| 4,599,361 | 7/1986 | Dickens et al. | 514/575 |
| 4,996,358 | 2/1991 | Handa et al. | 562/623 |

FOREIGN PATENT DOCUMENTS

| | | |
|---|---|---|
| 0012401 | 6/1980 | European Pat. Off. . |
| 0167936 | 1/1986 | European Pat. Off. . |
| 0214639 | 3/1987 | European Pat. Off. . |
| 0236872 | 9/1987 | European Pat. Off. . |
| 0274453 | 7/1988 | European Pat. Off. . |
| 3341610 A1 | 5/1984 | Germany . |

OTHER PUBLICATIONS

Woolley (1977), *Arthritis and Rheumatism,* vol. 20, pp. 1231–1239.
Cawston and Barrett (1979), *Anal. Biochem.,* vol. 99, pp. 340–345.
Cawston et al. (1981), *Biochem. J.,* vol. 195, pp. 159–165.
Cawston and Murphy (1981), *Methods in Enzymology,* vol. 80, pp. 711–721.
Amamoto et al. (1985), *Chemical Abstracts,* Abstract 130051c, vol. 102, p. 461.
Weller et al. (1984), *Biochem. and Biophy. Res. Comm.,* vol. 125, pp. 82–89.
Attwood, M.M. (1969), *Chemical Abstracts,* Abstract 85912s, vol. 70, p. 157.
Devlin et al. (1975), *J. Chem. Society,* Perkins Translation I, pp. 846–848.
Anderson et al. (1975), *J. Chem. Society,* Perkins Translation I, pp. 825–830.
Gordon et al. (1975), *J. Chem. Society,* Perkins Translation I, pp. 819–825.

*Primary Examiner*—Deborah C. Lambkin
*Assistant Examiner*—Ebenezer Sackey
*Attorney, Agent, or Firm*—Banner & Witcoff, Ltd.

[57] ABSTRACT

Compounds of general Formula I:

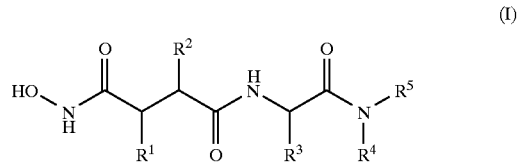

are presented which have collagenase inhibition activity and are useful in the management of disease involving tissue degradation and the promotion of wound healing. Representative diseases involving include arthropathy (particularly rheumatoid arthritis), inflammation, dermatological diseases, bone resorption disease and tumor invasion.

8 Claims, No Drawings

COMPOUNDS

This application is a divisional of Ser. No. 07/820,664, filed on Jan. 16, 1992, which is a 371 of PCT/GB90/01117 Jan. 16, 1992.

This invention relates to pharmaceutically and veterinarily active Hydroxamic Acid Based Collagenase Inhibitors, which are derivatives of hydroxamic acid.

The compounds of the present invention act as inhibitors of metalloproteases involved in tissue degradation, such as collagenase, which initiates collagen breakdown, stromelysin (protoglycanase), gelatinase and collagenase (IV). There is evidence implicating collagenase as one of the key enzymes in the breakdown of articular cartilage and bone in rheumatoid arthritis (*Arthritis and Rheumatism*, 20, 1231–1229, 1977). Potent inhibitors of collagenase and other metalloproteases involved in tissue degradation are useful in the treatment of rheumatoid arthritis and related diseases in which collagenolytic activity is important. Inhibitors of metalloproteases if of this type can therefore be used in treating or preventing conditions which involve tissue breakdown; they are therefore useful in the treatment of arthropathy, dermatological conditions, bone resorption, inflammatory diseases and tumour invasion and in the promotion of wound healing. Specifically, compounds of the present invention may be useful in the treatment of osteopenias such as osteoporosis, rheumatoid arthritis, osteoarthritis, periodontitis, gingivitis, corneal ulceration and tumour invasion.

A number of small peptide like compounds which inhibit netalloproteases have been described. Perhaps the most notable of these are those relating to the angiotensin converting enzyme (ACE) where such agents act to block the conversion of the decapeptide angiotensin I to angiotensin II a potent pressor substance. Compounds of this type are described in EP-A-0012401.

Certain hydroxamic acids have been suggested as collagenase inhibitors as in U.S. Pat. No. 4,599,361 and EP-A-0236872. Other hydroxamic acids have been prepared as ACE inhibitors, for example in U.S. Pat. No. 4,105,789, while still others have been described as enkephalinase inhibitors as in U.S. Pat. No. 4496540.

EP-A-0012401 discloses antihypertensive compounds of the formula:

$$R-\overset{O}{\underset{||}{C}}-\overset{R^1}{\underset{R^2}{\overset{|}{C}}}-NH-\overset{R^3}{\underset{|}{CH}}-\overset{R^4}{\underset{\underset{O}{||}}{\overset{|}{C}}}-N-\overset{R^5}{\underset{R^7}{\overset{|}{C}}}-\overset{O}{\underset{||}{C}}-R^6$$

wherein

R and $R^6$ are the same or different and are hydroxy, alkoxy, alkenoxy, dialkylamino alkoxy, acylamino alkoxy, acyloxy alkoxy, aryloxy, alkyloxy, substituted aryloxy or substituted aralkoxy wherein the substituent is methyl, halo, or nethoxy, amino, alkylamino, dialkylamino, aralkylamino or hydroxyamino;

$R^1$ is hydrogen, alkyl of from 1 to 20 carbon atoms, including branched, cyclic and unsaturated alkyl groups; substituted alkyl wherein the substituent is halo, hydroxy, alkoxy, aryloxy amino, alkylamino, dialkylamino, acrylamino, arylamino, guanidino, imidazolyl, indolyl, mercapto, alkylthio, arylthio, carboxy, carboxamido, carbalkoxy, phenyl, substituted phenyl wherein the substituent is alkyl, alkoxy or halo; aralkyl or heteroaralkyl, aralkenyl or heteroaralkenyl, substituted aralkyl, substituted heteroaralkyl, substituted aralkenyl or substituted hetereoaralkenyl, wherein the substituent is halor or dihalo, alkyl, hydroxy, alkoxy, amino, aminomethyl, acrylamino, dialkylamino, alkylamino, carboxyl, haloalkyl, cyano or sulphonamido, aralkyl or hetereoaralkyl substituted on the alkyl portion by amino or acylamino;

$R^2$ and $R^7$ are hydrogen or alkyl;

$R^3$ is hydrogen, alkyl, phenylalkyl, aminomethylphenylaikyl, hydroxyphenylalkyl, hydroxyalkyl, acetylaminoalkyl, acylaminoalkyl, acylaminoalkyl aminoalkyl, dimethylaminoalkyl, haloalkyl, guanidinoalkyl, imidazolylalkyl, indolylalkyl, mercaptoalkyl and alkylthioalkyl;

$R^4$ is hydrogen or alkyl;

$R^5$ is hydrogen, alkyl, phenyl, phenylalkyl, hydroxyphenylalkyl, hydroxyalkyl, aminoalkyl, guanidinoalkyl, imidazolylalkyl, indolylalkyl, mercaptoalkyl or alkylthioalkyl;

$R^4$ and $R^5$ may be connected together to form an alkylene bridge of from 2 to 4 carbon atoms, an alkylene bridge of from 2 to 3 carbon atoms and one sulphur atom, an alkylene bridge of from 3 to 4 carbon atoms containing a double bond or an alkylene bridge as above, substituted with hydroxy, alkoxy or alkyl and the pharmaceutically acceptable salts thereof.

U.S. Pat. No. 4,599,361 discloses compounds of the formula:

$$HOHNC\overset{O}{\underset{||}{-}}A-\overset{O}{\underset{||}{C}}NH-\overset{R^2}{\underset{a}{\overset{|}{C}H}}-\overset{O}{\underset{||}{C}}NHR^1$$

wherein $R^1$ is $C_1$–$C_6$ alkyl;

$R^2$ is $C_1$–$C_6$ alkyl, benzyl, benzyloxybenzyl, ($C_1$–$C_6$ alkoxy) benzyl or benzyloxy($C_1$–$C_6$ alkyl);

a is a chiral centre with optional R or S stereochemistry;

A is a $$-\underset{b}{(CHR^3}-\underset{c}{CHR^4)}-\text{group}$$

or a —($CR^3$=$CR^4$)— group wherein b and c are chiral centres with optional R or S stereochemistry;

$R^3$ is hydrogen, $C_1$–$C_6$ alkyl, phenyl or phenyl($C_1$–$C_6$ alkyl) and $R^4$ is hydrogen, $C_1$–$C_6$ alkyl, phenyl($C_1$–$C_6$ alkyl), cycloalkyl or cycloalkyl($C_1$–$C_6$ alkyl).

EP-A-0236872 discloses generically compounds of the formula $$\overset{A}{\underset{R^3}{\overset{|}{H}C}}-\overset{R^1}{\underset{|}{CH}}-CO-NH-\overset{R^2}{\underset{|}{CH}}-CO-\overset{}{\underset{R^6}{\overset{|}{N}}}-\overset{R^4}{\underset{|}{CH}}-R_5$$

wherein

A represents a group of the formula HN(OH)—CO— or HCO—N(OH)—;

$R^1$ represents a $C_2$–$C_5$ alkyl group;

$R^2$ represents the characterising group of a natural alpha-amino acid in which the functional group can be protected, amino groups may be acylated and carboxyl groups can be amidated, with the proviso that $R^2$ can not represent hydrogen or a methyl group;

$R^3$ represents hydrogen or an amino, hydroxy, mercapto, $C_1$–$C_6$ alkyl, $C_1$–$C_6$ alkoxy, $C_1$–$C_6$ acylamino, $C_1$–$C_6$-alkylthio, aryl-($C_1$–$C_6$ alkyl) -, amino-($C_1$–$C_6$-alkyl) hydroxy($C_1$–$C_6$-alkyl) -, mercaptco($C_1$–$C_6$ alkyl) or carboxy($C_1$–$C_6$ alkyl) group, wherein the amino, hydroxy, mercapto or carboxyl groups can be protected and the amino groups may be acylated or the carboxyl groups may be amidated;

$R^4$ represents hydrogen or a methyl group;

$R^5$ represents hydrogen or a $C_1$–$C_6$ acyl, $C_1$–$C_6$ alkoxy-$C_1$–$C_6$ alkyl, di($C_1$–$C_6$-alkoxy)methylene, carboxy, ($C_1$–$C_6$ alkyl)carbinyl, ($C_1$–$C_6$ alkoxy) carbinyl, aryl-methoxy carbinyl, ($C_1$–$C_6$ alkyl)amino carbinyl or arylamino carbinyl group; and $R^6$ represents hydroxy or a methylene group; or $R^2$ and $R^4$ together represent a group-$(CH_2)_n$—, wherein n represents a number from 4 to 11; or $R^4$ and $R^5$ together represent a trimethylene group;

and pharmaceutically acceptable salts of such compounds, which are acid or basic.

U.S. Pat. No. 4,105,789 generically discloses compounds which have the general formula

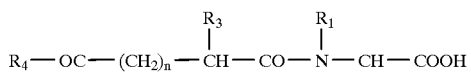

and salts thereof, wherein $R_1$ is hydrogen, lower alkyl, phenyl lower alkylene, hydroxy-lower alkylene, hydroxyphenyl lower alkylene, amino-lower alkylene, guanidine lower alkylene, mercapto-lower alkylene, lower alkyl-mercapto-lower alkylene, imidazolyl lower alkylene, indolyl-lower alkylene or carbamoyl lower alkylene;

$R_2$ is hydrogen or lower alkyl;

$R_3$ is lower alkyl or phenyl lower alkylene;

$R_4$ is hydroxy, lower alkoxy or hydroxyamino; and n is 1 or 2.

U.S. Pat. No. 4,496,540 discloses compounds of the general formula:

wherein A is one of the aromatic group-containing amino acid residues L-tryptophyl, D-tryptophyl, L-tyrosyl, D-tyrosyl, L-phenylalanyl, or D-phenylalanyl, and B is one of the amino acids glycine, L-alanine, D-alanine, L-leucine, D-leucine, L-isoleucine, or D-isoleucine; and pharmaceutically acceptable salts thereof.

It would be desirable to improve on the solubility of known collagenase inhibitors and/or stromelysin inhibitors (whether as the free base or the salt) and, furthermore, increases in activity have also been sought. It is not a simple matter, however, to predict what variations in known compounds would be desirable to increase or even retain activity; certain modifications of known hydroxamic acid derivatives have been found to lead to loss of activity.

According to a first aspect of the invention, there is provided a compound of general formula I:

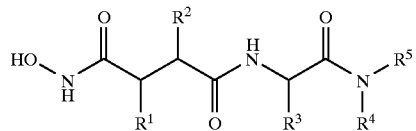

wherein:

$R^1$ represents a hydrogen atom or a $C_1$–$C_6$ alkyl, $C_1$–$C_6$ alkenyl, phenyl, phenyl($C_1$–$C_6$)alkyl, $C_1$–$C_6$ alkylthiomethyl, phenylthiomethyl, substituted phenylthiomethyl, phenyl($C_1$–$C_6$)alkylthiomethyl or heterocyclylthiomethyl group; or $R^1$ represents —S—$R^x$ wherein $R^x$ represents a group

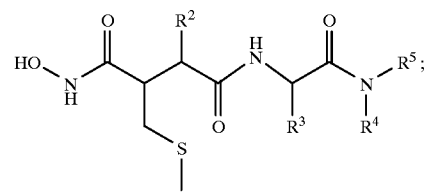

$R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl, or cycloalkenyl($C_1$–$C_6$)alkyl;

$R^3$ represents an amino acid side chain or a $C_1$–$C_6$ alkyl, benzyl, ($C_1$–$C_6$)alkoxybenzyl, benzyloxy($C_1$–$C_6$)alkyl or benzyloxybenzyl group;

$R^4$ represents a hydrogen atom or a methyl group;

$R^5$ represents a group $(CH_2)_n$A;

n is an integer from 1 to 6; and

A represents a hydroxy, ($C_2$–$C_7$)acyloxy, ($C_1$–$C_6$) alkylthio, phenylthio, ($C_2$–$C_7$)acylamino or N-pyrrolidone group or a salt and/or N-oxide and/or (where the compound is a thio-compound) a sulphoxide or sulphone thereof.

Hereafter in this specification, the term "compound" includes "salt" unless the context requires otherwise.

As used herein the term "$C_1$–$C_6$ alkyl" refers to a straight or branched chain alkyl moiety having from one to six carbon atoms, including for example, methyl, ethyl, propyl, isopropyl, butyl, t-butyl, pentyl and hexyl, and cognate terms (such as "$C_1$–$C_6$ alkoxy") are to be construed accordingly.

The term "$C_1$–$C_6$ alkenyl" refers to a straight or branched chain alkyl moiety having one to six carbons and having in addition one double bond, of either E or Z stereochemistry where applicable. This term would include, for example, an alpha, beta-unsaturated methylene, vinyl, 1-propenyl, 1- and 2-butenyl and 2-methyl-2-propenyl.

The term "cycloalkyl" refers to a saturated alicyclic moiety having from 3 to 8 carbon atoms and includes, for example, cyclopropyl, cyclobutyl, cyclopentyl and cyclohexyl.

The term "cycloalkenyl" refers to an unsaturated alicyclic moiety having from 3 to 8 carbon atoms and includes, for example, cyclopropenyl, cyclobutenyl, cyclopentenyl and cyclohexenyl.

The term "heterocyclylthiomethyl" refers to a methyl group substituted by a hetrocyclic thiol for example pyridine-2-thiol, pyridine-4-thiol, thiophene-2-thiol or pyrimidine-2-thiol.

The term "substituted", as applied to a phenyl or other aromatic ring, means substituted with up to four substituents each of which independently may be $C_1$–$C_6$ alkyl, $C_1$–$C_6$ alkoxy, hydroxy, thiol, $C_1$–$C_6$ alkylthiol, amino, halo (including fluoro, chloro, bromo and iodo), triflouromethyl, nitro, —COOH, —COONH$_2$ or —CONHR$^A$, wherein R$^A$ represents a $C_1$–$C_6$ alkyl group or the characteristic side chain of an amino acid such as alanine, valine, leucine, isoleucine, phenylalanine, tryptophan, methionine, glycine, serine, threonine, cysteine, tyrosine, asparagine, glutamine, aspartic acid, glutamic acid, lysine, arginine or histidine.

The term "amino acid side chain" means a characteristic side chain attached to the —CH(NH$_2$)(COOH) moiety in the following R or S amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

There are several chiral centres in the compounds according to the invention because of the presence or asymmetric carbon atoms. The presence of several asymmetric carbon atoms gives rise to a number of diastereomers with the appropriate R or S stereochemistry at each chiral centre. General formula I and, where appropriate, all other formulae in this specification are to be understood to include all such stereoisomers and mixtures (for example racemic mixtures) thereof. Compounds in which the chiral centre adjacent the substituent R$^3$ has S stereochemistry are preferred.

Further or other preferred compounds include those in which, independently or in any combination:

R$^1$ represents a hydrogen atom or a $C_1$–$C_4$ alkyl (such as methyl), phenylthiomethyl or heterocyclylthiomethyl (such as thiophenylthiomethyl) group;

R$^2$ represents a $C_3$–$C_6$ alkyl (such as isobutyl or n-pentyl) group:

R$^3$ represents a benzyl, 4-($C_1$–$C_6$)alkoxyphenylmethyl or benzyloxy benzyl group;

R$^4$ represents a hydrogen atom;

n has the value 1, 2 or 3; and/or

A represents a hydroxy, acetoxy, acetylamino, ethylthio or N-pyrrolidone group.

Particularly preferred compounds include:
1. [4-(N-Hydroxyamino)-2R-isobutylsuccinyl]-L-phenylalanine-N-(2-hydroxyethyl)-amide;
2. [4-(N-Hydroxyamino)-2R-isobutylsuccinyl]-L-phenylalanine-N-(2-hydroxyethyl)-N-methylamide;
3. [4-(N-Hydroxyamino)-2R-isobutylsuccinyl]-L-phenylalanine-N-(2-ethyl thioethyl) amide;
4. [4-(N-Hydroxyamino)-2R-isobutylsuccinyl]-L-phenylalanine-N-(2-N-acetyl-2-aminoethyl) amide;
5. [4-(N-Hydroxyamino)-2R-isobutylsuccinyl]-L-phenylalanine-N-(3-(2-pyrrolidone)propyl) amide;
6. [4-(N-Hydroxyamino)-2R-isobutylsuccinyl]-L-phenylalanine-N-(3-(2-pyrrolidone)propyl) amide sodium salt;
7. [4-(N-Hydroxyamino)-2R-isobutylsuccinyl]-L-phenylalanine-N-(2-acetoxyethyl) amide;
8. [4-(N-Hydroxyamino)-2R-isobutyl-3S-methylsuccinyl]-L-phenylalanine-N-(3-(2-pyrrolidone)propyl) amide;
9. [4-(N-Hydroxyamino)-2R-isobutyl-3S-methylsuccinyl]-L-phenylalanine-N-methyl-N-(2-hydroxyethyl) amide;
10. [4-(N-Hydroxyamino)-2R-isobutyl-3S-methylsuccinyl]-L-phenylalanine-N-(2-hydroxyethyl) amide;
11. [4-(N-Hydroxyamino)-2R-isobutyl-3S-methylsuccinyl]-L-phenylaianine-N-(3-(2-pyrrolidone)propyl) amide sodium salt;

and free bases, free acids and salts thereof, where appropriate. Compounds 8 and 5 are especially preferred and compound 8 is the most preferred.

Compounds of general formula I may be prepared by any suitable method known in the art and/or by the following process, which itself forms part of the invention.

According to a second aspect of the invention, there is provided a process for preparing a compound of general formula I as defined above, the process comprising:

(a) deprotecting (for example by hydrogenating) a compound of general formula III

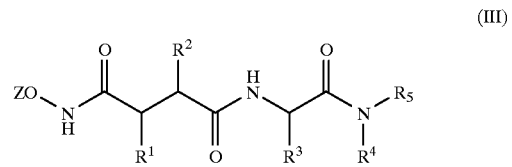

(III)

wherein:
R$^1$, R$^2$, R$^3$, R$^4$ and R$^5$ are as defined in general formula I and Z represents a protective group, such as a benzyl group; or (b) reacting a compound of general formula IV

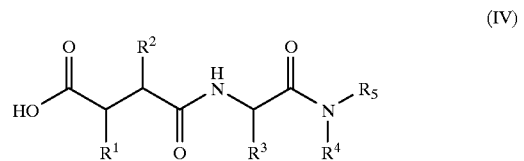

(IV)

wherein:
R$^1$, R$^2$, R$^3$, R$^4$ and R$^5$ are as defined in general formula I, with hydroxylamine or a salt thereof; and (c) optionally after step (a) or step (b) converting a compound of general formula I into another compound of general formula I.

Compounds of general formula I which are sulphoxides or sulphones can be derived from thiol compounds of general formula I by oxidation. Alternatively, thiols of general formula III or IV can be oxidised.

Compounds of general formula I which are disulphide (ie compounds wherein R$^1$ represents SR$^x$) may be derived from thiol compounds of general formula I by mild oxidation with, for example, iodine in methanol.

A compound of general formula III can be obtained by coupling, for example by conventional coupling techniques, a compound of general formula IV with an O-protected (for example benzyl) hydroxylamine or by reacting a compound of general formula V

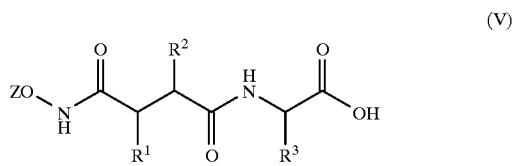

(V)

wherein:
R$^1$, R$^2$ and R$^3$ are as defined in general formula I and Z represents a protective group such as benzyl, with a compound of general formula VI

NHR⁴R⁵ (VI)

A compound of general formula V may be prepared by hydrolysis in the presence of a base such as sodium hydroxide of a compound of general formula VII

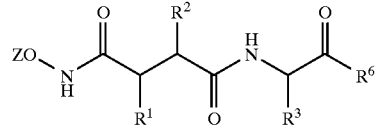

(VII)

wherein:

R¹, R² and R³ are as defined in general formula I, R⁶ represents a $C_1$–$C_6$ alkoxy, benzyloxy or substituted (eg 4-nitro) benzyloxy group, and Z represents a protective group.

A compound of general formula VII may be prepared by coupling, for example by conventional coupling techniques, a compound of general formula VIII with an O-protected (for example benzyl) hydroxylamine

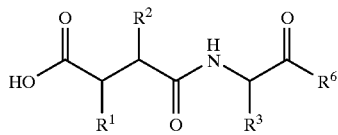

(VIII)

wherein:

R¹, R² and R³ are as defined in general formula I and R⁶ represents a $C_1$–$C_6$ alkoxy, benzyloxy or substituted benzyloxy group.

A compound of general formula VIII may be prepared by hydrogenating and (eg thermally) decarboxylating a compound of general formula IX

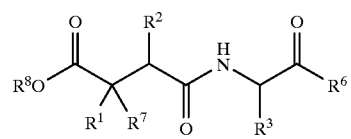

(IX)

wherein:

R¹, R² and R³ are as defined in general formula I, R⁸ represents a $C_1$–$C_6$ alkyl or benzyl group, R⁶ represents a $C_1$–$C_6$ alkoxy, benzyloxy or substituted benzyloxy group and R⁷ represents a $C_1$–$C_6$ alkoxycarbonyl or benzyloxycarbonyl group.

A compound of general formula IX may be prepared by reacting a substituted acid of general formula X

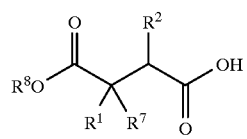

(X)

wherein:

R¹ and R² are as defined in general formula I, R⁸ represents a $C_1$–$C_6$ alkyl or benzyl group and R⁷ represents a $C_1$–$C_6$ alkoxycarbonyl or benzyloxycarbonyl group, with an amino acid derivative of general formula (XI)

wherein:

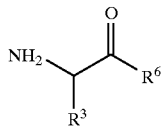

(XI)

R³ is as defined in general formula I and R⁶ represents a $C_1$–$C_6$ alkoxy, benzyloxy or substituted benzyloxy group.

Alternatively, a compound of general formula IV can be prepared by de-esterifying (for example hydrolysing, under acid or base catalysis) a compound of general formula XII

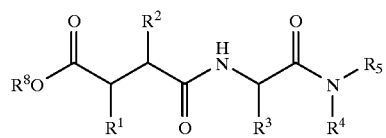

(XII)

wherein:

R¹, R², R³, R⁴ and R⁵ are as defined in general formula I and R³ represents a $C_1$–$C_6$ alkyl or benzyl group.

A compound of general formula XII can be prepared in a manner analogous to the preparation of a compound of formula IX by reacting a substituted acid of general formula XIII

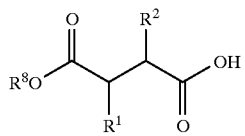

(XIII)

wherein:

R¹ and R² are as defined in general formula I and R₈ represents a $C_1$–$C_6$ alkyl or benzyl group, with an amino acid derivative of general formula XIV

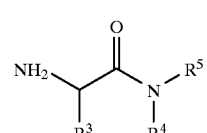

(XIV)

wherein:

R³, R⁴ and R⁵ are as defined in general formula I.

In a further synthetic variant, a compound of general formula X as defined above wherein R¹ represents a hydrogen atom can be reacted with a compound of general formula XIV to produce a compound of general formula XV

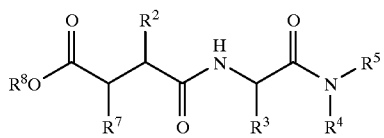

(XV)

wherein:

$R^2$, $R^3$, $R^4$ and $R^5$ are as defined in general formula I, $R^8$ represents a $C_1$–$C_6$ alkyl or benzyl group and $R^7$ represents a $C_1$–$C_6$ alkoxycarbonyl or benzyloxycarbonyl group.

A compound of general formula XV wherein $R^8$ represents benzyl and $R^1$ represents benzyloxycarbonyl may be hydrogenated to the malonic acid, then treatment with aqueous formaldehyde and piperidine gives a compound of formula XVI

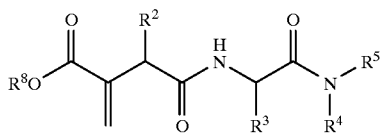

(XVI)

wherein:

$R^2$, $R^3$, $R^4$ and $R^5$ are as defined in general formula I.

Compounds of general formula XVI, by treatment with the appropriate thiols give the acids of general formula IV where $R^1$ is a substituted thiomethyl derivative. Thiomethyl derivatives can be oxidised to sulphoxides and sulphones as appropriate.

The starting materials (compounds of general formulae IX, X, XIII and XIV) and reagents described above are either commercially available or may be produced by conventional processes from commercially available materials. For example, when $R^1$ represents a hydrogen atom, the substituted acid of general formula XIII may be prepared by reaction of an aldehyde XVII $R^9$CHO    (XVII)

wherein $R^9$ represents a hydrogen atom or a $C_1$–$C_5$ alkyl $C_1$–$C_5$ alkenyl, phenyl ($C_1$–$C_5$) alkyl, cycloalkyl ($C_{-C5}$) alkyl or cycloalkenyl ($C_1$–$C_5$) alkyl group, with a succinate derivative of general formula XVIII,

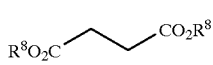

(XVIII)

wherein:

$R^8$ represents a $C_1$–$C_6$ alkyl or benzyl group under base catalysis to give a mixture of acids of general formulae XIXa and XIXb

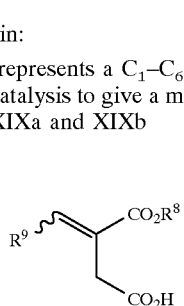

(XIXa)

(XIXb)

which by hydrogenation, esterification and hydrolysis can be converted to the acids of the general formula XIII.

Alternatively an ester of general formula XX may be reacted with an ester stablised phosphorane of general formula XXI.

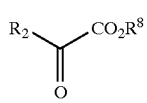

(XX)

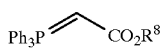

(XXI)

to yield a compound of general formula XXII

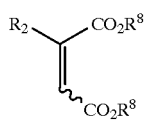

(XXII)

wherein $R^8$ represents a $C_1$–$C_6$ alkyl group, which can be further converted by hydrogenation to the acids of general formula XIII.

In addition the substituted esters may be prepared by reacting an ester of the general formula XXIII

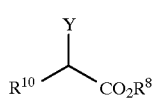

(XXIII)

wherein Y represents halo and $R^8$ is as defined above and $R^{10}$ is either $R^1$ or $R^2$ as defined above, with a malonate derivative of the general formula XXIV

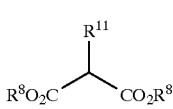

(XXIV)

wherein $R^{11}$ is $R^2$ or $R^1$ as defined above, and the alternative to that substituent employed in the halo ester.

Compounds of general formulae III and IV are valuable intermediates in the preparation of compounds of general formula I. According to a third aspect of the invention, there is therefore provided a compound of general formula III. According to a fourth aspect of the invention, there is provided a compound of general formula IV.

As mentioned above, compounds of general formula I are useful in human or veterinary medicine as they are active inhibitors, of metalloproteases involved in tissue degradation.

According to a fifth aspect of the invention, there is provided a compound of general formula I for use in human or veterinary medicine, particularly in the management (by which is meant treatment of prophylaxis) of disease involving tissue degradation, in particular rheumatoid arthritis, and/or in the promotion of wound healing.

According to a sixth aspect of the invention, there is provided the use of a compound of general formula I in the preparation of an agent for the management of disease involving tissue degradation, particularly rheumatoid arthritis, and/or in the promotion of wound healing. Compounds of general formula I can therefore be used in a method of treating disease involving tissue degradation, particularly rheumatoid arthritis, and/or in a method of promoting wound healing, the method in either case comprising administering to a human or animal patient an effective amount of a compound of general formula I.

The potency of compounds of general formula I to act as inhibitors of collagenase (a metalloprotease involved in tissue degradation) was determined by the procedure of Cawston and Barrett, (*Anal. Biochem.*, 99, 340–345, 1979) and their potency to act as inhibitors of stromelysin was determined using the procedure of Cawston et al (*Biochem. J.*, 195, 159–165 1981), both of which techniques are to be described more fully in the examples and, to the extent that the law allows, are incorporated by reference herein.

According to a seventh aspect of the invention, there is provided a pharmaceutical or veterinary formulation comprising a compound of general formula I and a pharmaceutically and/or veterinarily acceptable carrier. One or more compounds of general formula I may be present in association with one or more non-toxic pharmaceutically and/or veterinarily acceptable carriers and/or diluents and/or adjuvents and if desired other active ingredients.

According to an eighth aspect of the invention, there is provided a process for the preparation of a pharmaceutical or veterinary formulation in accordance with the seventh aspect, the process comprising admixing a compound of general formula I and a pharmaceutically and/or veterinarily acceptable carrier.

Compounds of general formula I may be formulated for administration by any route and would depend on the disease being treated. The may be in the form of tablets, capsules, powders, granules, lozenges, liquid or gel preparations, such as oral, nasal, topical, or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrollidone; fillers for example lactose, sugar, maize-starch, calcium phosphate, sorbitol or glycine; tableting lubricant, for example magnesium sterate, talc, polyethylene glycol or silica; disintegrants, for example potato starch, or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia: non-aqujeous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg, of a compound of general formula I. A suitable daily dose for a mammal may vary widely depending on the condition of the patient and will ultimately depend on the judgement of the physician or veterinarian. However, a dose of a compound of general formula I of about 0.1 to 300 mg/kg body weight, particularly from about 1 to 100 mg/kg body weight may be appropriate.

For topical application to the skin the drug may be made up into a cream, lotion or ointment. Cream or ointment formulations that may be used for the drug are conventional formulations well known in the art, for example, as described in standard text books of pharmaceutics such as the British Pharmacopoeia.

For topical applications to the eye, the drug may be made up into a solution or suspension in a suitable sterile aqueous or non-aqueous vehicle. Additives, for instance buffers such as sodium metabisulphite or disodium edeate; preservatives including bactericidal and fungicidal agents, such as phenyl mercuric acetate or nitrate, benzalkonium chloride or chlorohexidine, and thickening agents such as hypromellose may also be included.

The dosage employed for the topical administration will, of course, depend on the size of the area being treated. For the eyes each dose will be typically in the range from 10 to 100 mg of the compound of general formula I.

The active ingredient may also be administered parenterally in a sterile medium. The drug depending on the vehicle and concentration used, can either be suspended or dissolved in the vehicle. Advantageously, adjuvants such as a local anaesthetic, preservative and buffering agents can be dissolved in the vehicle.

For use in the treatment of rheumatoid arthritis the compounds of this invention can be administered by the oral route or by injection intra-articularly into the affected joint. The daily dosage for a 70 kg mammal will be in the range of 10 mg to 1 gram of a compound of general formula I.

The following examples illustrate the invention, but are not intended to limit the scope in any way.

The following abbreviations have been used in the Examples:

DCC—Dicyclohexylcarbodiimide
DCM—Dichloromethane
DCU—Dicyclohexylurea
DIPE—Diisopropyl ether
DMF—N,N-dimethyiformamide
HOBT—Hydroxybenztriazole
NMM—N-Methylmorpholine
TFA—Trifluoroacetic acid
THF—Tetrahydrofuran
WSCDI—N-(Dimethylaminoethyl)-N'-ethylcarbodiimide

EXAMPLES

EXAMPLE 1

[4-(N-Hydroxyamino)-2R-isobutylsuccinyl]-L-phenylalanine-N-(2-hydroxyethyl)-amide

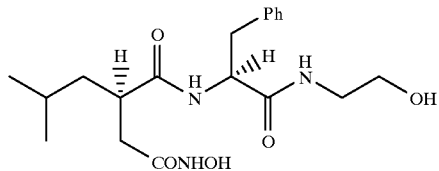

(a) [4-Benzyloxy-3-benzyloxycarbonyl-2R-isobutylsuccinyl]-L-phenylalanine methyl ester Benzyl (2-benzyloxycarbonyl-5-methyl-3R-tert-butoxycarbonyl)-hexanoate (52 g, 115 mmol) was stirred at room temperature with 5% water in TFA (250 ml) for 1.5 h. After this time the TFA was evaporated under reduced pressure then the residue was azeotroped with toluene (3×250 ml).

The crude acid from this reaction was dissolved in DCM/DMF (4:1), then HOBT (16 g, 118 mmol), NMM (12 g, 118 mmol) and WSCDI (22 g, 115 mmol) were added at room temperature. After 20 minutes a further equivalent of NMM (12 g, 118 mmol) was added followed by L-phenylalanine methyl ester hydrochloride (23 g, 107 mmol). This solution was stirred overnight and then concentrated under vacuum. The oily residue was dissolved in DCM then washed with 10% citric acid (2×250 ml), with 10% sodium bicarbonate (2×250 ml) and once with saturated brine (250 ml). The organic layer was dried (sodium sulphate), filtered then the solvent removed under reduced pressure to give the title compound as an oil (50.9 g, 79%).

$\delta_H$ (250 MHz, CDCl$_3$, 3:1 mixture of diastereomers) Major diastereomer 0.72 (3H, d, J=6 Hz, CH(CH$_3$)$_2$), 0.74 (3H, d, J=6 Hz, CH(CH$_3$)$_2$), 0.80–1.00 (2H, m, CHCH$_2$+CHMe$_2$), 1.40–1.60 (2H, m, CHCH$_2$+CHCH$_2$), 2.95 (1H, dd, J=14,6 Hz, CH$_2$Ph), 3.07 (1H, dd, J=14,5 Hz, CH$_2$Ph), 3.64 (3H, s, CO$_2$Me), 3.82 (1H, d, J=10 Hz, CH(CO$_2$Bn)$_2$), 4.82 (1H, m, CHCO), 5.0–5.2 (2H, m, OCH$_2$Ph), 6.2 (1H, d, J=8 Hz, NH), and 7.10–7.40 (15H, m, Ph). Minor diastereomer shows 0.63 (3H, d, J=6 Hz, CH(CH$_3$)$_2$) , 0.68 (3H, d, J=6 Hz, CH(CH$_3$)$_2$), 3.67 (3H, s, CO$_2$Me), and 3.75 (1H, d, J=8 Hz, CH(CO$_2$Bn)$_2$)

(b) [4-Hydroxy-2R-isobutylsuccinyl]-L-phenylalanine methyl ester

The product from above (50.9 g, 91 mmol) was dissolved in ethanol (100 ml) and stirred at room temperature with activated charcoal pellets for 1 h. 10% Palladium on charcoal (20 g) in ethyl acetate was slurried into the ethanolic solution. Cyclohexene (20 ml) in ethanol (100 ml) was added and the mixture was brought to reflux for 5 h. The reaction mixture was filtered to remove the catalyst, then the solvents evaporated under reduced pressure to leave a yellow oil (29.8 g). This oil was taken up in xylene (500 ml) and heated at reflux for 10 minutes. The xylene was removed under reduced pressure to leave the crude material as an oil (26.5 g).

(c) [4-(N-Benzyloxyamino)-2R-isobutylsuccinyl]-L-phenylalanine methyl ester

The crude acid (26.5 g, 79 mmol) was dissolved in DCM/DMF (4:1, 500 ml), then NMM (9.6 g, 95 mmol), HOBT (12.8 g 95 mmol) and WSCDI (18.2 g, 95 mmol) added and the mixture stirred at room temperature until tlc indicated complete conversion to the activated ester (about 10 minutes). To this solution containing the active ester was added benzylhydroxylamine hydrochloride (15.2 g, 95 mmol) and a further equivalent of NMM (9.6 g, 95 mmol) in the solvent mixture (80 ml). After stirring at room temperature overnight DCM (250 ml) was added then the mixture washed with citric acid (2×250 ml), 10% sodium bicarbonate solution (2×250 ml) and brine (250 ml) then finally dried over sodium sulphate. The solution was filtered and the solvent removed under reduced pressure to give an oil (27.2 g) which was purified by column chromatography using ether as an eluant to give the title compound (11 g, 23.7 mmol, 30%).

$\delta_H$ (250 MHz, CDCl$_3$) 0.84 (6H, m, CH(CH$_3$)$_2$), 1.16 (1H, m, CHMe$_2$), 1.51 (2H, m, CH$_2$CHMe$_2$), 2.1–2.4 (2H, bm, CH$_2$CONHOBn), 2.73 (1H, m, CH$_2$CHCO), 3.06 (2H, d, J=6 Hz, CH$_2$Ph), 3.68 (3H, s, CO$_2$Me), 4.8–5.0 (3H, s+m, OCH$_2$Ph and COCHNH), 6.25 (1H, d, J=8 Hz, NH), 7.05–7.50 (10H, m, Ph), and 8.66 (1H, s, NHOBn).

(d) [4-(N-Benzyloxyamino)-2R-isobutylsuccinyl]-L-phenylalanine

[4-(N-Benzyloxyamino)-2R-isobutylsuccinyl]-L-phenylalanine methyl ester (9.5 g, 21 mmol) was dissolved in methanol (200 ml) and lithium hydroxide solution (0.5N, 84 ml, 42 mmol) was added with stirring at room temperature. When the reaction was complete, as judged from tlc, the methanol was removed by evaporation and the remaining aqueous phase was acidified to pH1 with citric acid. The precipitated solid was filtered off and dried, while the fitrate was extracted with DCM (500 ml) and dried over sodium sulphate. Solvent removal from the organic phase left an oil (5.38 g) which could be recrystallised from diisopropyl ether and methanol to give material which was identical with the solid which precipitated during acidification. These two batches were combined to give the title compound (6.40 g, 15 mmol, 71%)

m.p. 161–162° C.

nu$_{max}$(KBr) 3300, 3020, 2980, 1710, 1650, 1630, 1550, 1265, 740, and 700 cm$^{-1}$ $\delta_H$ (250 MHz, CDCl$_3$/D$_6$-DMSO) 0.80–0.87 (7H, m), 1.50 (2H, bm), 2.0–2.1 (2H, m), 2.91–3.14 (2H, m, CH$_2$Ph), 4.77 (2H, s, OCH$_2$Ph), and 7.18–7.36 (10H, m, Ph).

$\delta_C$ (62.9 MHz, D$_6$-DMSO) 174.1, 173.1, 167.7, 137.9, 129.2–126.4, 76.9, 53.3, 40.7, 39.9, 36.8, 35.8, 25.3, 23.5, and 22.1

(e) [4-(N-Hydroxyamino)-2R-isobutylsuccinyl]-L-phenylalanine-N-(2-hydroxyethyl)-amide

[4-(N-Benzyioxyamino)-2R-isobutylsuccinyl]-L-phenylalanine (7.50 g, 17.6 mmol) was dissolved in DCM (100 ml) and cooled in ice. Triethylamine (1.96 g, 19.4 mmol) was added together with ethylchloroformate (2.10 g, 19.4 mmol) and after 10 minutes ethanolamine (1.55 g, 21.1 mmol) in DCH (10 ml) was added. After 3 h at room temperature the reaction mixture was diluted with ethyl acetate then washed with sodium bicarbonate solution and brine, and finally dried over sodium sulphate. Solvent removal under reduced pressure gave the crude benzyl hydroxamate which was recrystallised from ethyl acetate/hexane (2.6 g, 5.5 mmol)

The crude material from above was dissolved in cyclohexene/ethanol (10% solution, 55 ml), 10% palladium on charcoal (250 mg) was added then the mixture refluxed until starting material had dissappeared by tlc (ca. 30 minutes). The catalyst was removed by filtration, and the solvent removed under reduced pressure to leave a solid which could be recrystallised from methanol and DIPE. The required product (1.54 g, 4.00 mmol, 74%) was collected by filtration.

m.p. 156–158° C.

[α]$_D$=−21.5 (c=1, MeOH)

nu$_{max}$(KBr) 3300, 2950, 1650, 1550, and 700 cm$^{-1}$

δ$_H$ (250 MHz, CDCl$_3$) 0.72 (3H, d, J=6 Hz, CH(CH$_3$)$_2$), 0.77 (3H, d, J=6 Hz, CH(CH$_3$)$_2$), 0.95 (1H, m, CHCH$_2$), 1.28 (2H, m, CH(CH$_3$)$_2$+CHCH$_2$), 1.92 (2H, m, CH$_2$CONHOH), 2.61 (1H, bm, CHCO), 2.80 (1H, dd, J=14, 12 Hz, CH$_2$Ph), 3.00–3.20 (3H, m, NCH$_2$+CH$_2$Ph), 4.41 (1H, m, NCHCO), 4.65 (1H, bt, OH), 7.22 (5H, m, Ph), 7.86 (1H, t, J=6 Hz, CONHCH$_2$), 8.07 (1H, d, J=8 Hz, CONH), and (8.76 (1H, s, NHOH).

δ$_C$ (62.9 MHz, D$_6$-DMSO) 174.0, 171.2, 138.3, 129.2, 128.1, 126.2, 59.8, 54.0, 41.6, 37.3, 35.8, 25.3, 23.5, and 22.0.

Analysis calculated for C$_{19}$H$_{29}$N$_3$O$_5$ Requires C 60.14H 7.70N 11.07 Found C 59.97H 7.68N 11.10

EXAMPLE 2

[4-(N-Hydroxyamino)-2R-isabutylsuccinyl]-L-phenylalanine-N-(2-hydroxyethyl)-N-methylamide.

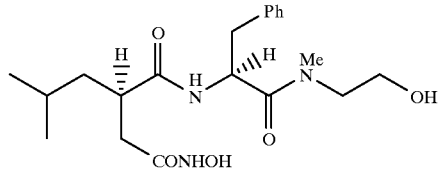

Using the procedure described in Example 1e [4-(N-Benzyloxyamino)-2R-isobutylsuccinyl]-L-phenylalanine (0.5 g, 1.17 mmol ) was coupled with N-methylethanolamine (100 mg, 1.29 mmol) then the product hydrogenated to give the title compound (97 mg, 0.25 mmol, 21%)

m.p. 136.0–137.0° C.

[α]$_D$=+1.1 (c=1, MeOH)

nu$_{max}$(KBr) 3600–3100, 2960, 1680, 1560, 940, 750, and 700 cm$^{-1}$

δ$_H$(250 MHz, CDCl$_3$/D$_6$-DMSO, 1:1) 0.74 (6H, m, CH(CH$_3$)$_2$), 1.00 (1H, m, CH$_2$CHMe$_2$), 1.36 (2H, m, CH$_2$CHMe$_2$), 2.00 (2H, m, CH$_2$NHOH), 2.60–3.00 (3H, m, +3H, 2×s), 3.39 (2H, m), 4.42–4.70 (1H, m, OH), 4.80–5.00 (1H, m, CH$_2$Ph), 7.14 (5H, m, Ph), 7.97 (1H, d, J=7 Hz, NH), and 8.50 (1H, s, NHOH)

δ$_C$ (62.9 MHz, D$_6$-DMSO, 1:1 Mixture of Rotamers) 173.9, 173.8, 171.3, 170.3, 167.5, 138.2, 137.9, 129.4, 128.1, 126.4, 126.3, 58.7, 58.4, 51.2, 50.2, 50.0, 49.7, 40.7, 40.5, 39.8, 37.7, 37.4, 36.0, 35.9, 33.9, 25.4, 23.5, 23.4, and 22.1.

EXAMPLE 3

[4-(N-Hydroxyamino)-2R-isobutylsuccinyl]-L-phenylalanine-N-(2-ethyl thioethyl) amide.

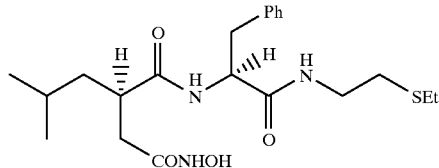

Using the procedure described in Example 1e 4-(N-Benzyloxyamino)-2R-isobutylsuccinyl]-L-phenylalanine (0.5 g, 1. 17 mmol) was coupled with 2-(thioethyl)-1-aminoethane hydrochloride (183 mg, 1.29 mmol) then the product hydrogenated to give the title compound (163 mg).

m.p. 169–171° C.

[α]$_D$=−19.7° (c=1, MeOH)

nu$_{max}$(KBr) 3280, 2950, 2920, 1655, 1640, and 1540 cm$^{-1}$

δ$_H$ (250 MHz, D$_6$-DMSO) 0.72 (3H, d, J=6 Hz), 0.77 (3H, d, J=7 Hz), 0.95 (1H, m), 1.17 (3H, t, J=7 Hz), 1.29 (2H, m), 1.93 (2H, m), 2.49 (4H, m), 2.62 (1H, m), 2.82 (1H, dd, J=14,10 Hz), 3.03 (1H, dd, J=14,5 Hz), 3.19 (2H, m), 4.40 (1H, m), 7.22 (5H, m), 8.07 (2H, m), 8.75 (1H, s), and 10.39 (1H, s).

δ$_C$ (62.9 MHz, D$_6$-DMSO) 174.0, 171.1, 167.7, 138.3, 129.2, 128.1, 126.3, 54.1, 40.8, 40.7, 38.8, 37.3, 35.8, 30.0, 25.3, 24.9, 23.5, 22.0, and 14.9.

EXAMPLE 4

[4-(N-Hydroxyamino)-2R-isobutylsuccinyl]-L-phenylalanine-N-(2-N-acetylethyl) amide.

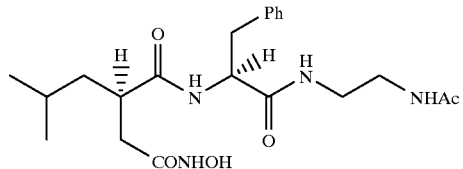

Using the procedure described in Example 1e [4-(N-Benzyloxyamino)-2R-isobutylsuccinyl]-L-phenylalanine (0.43 g, 1.0 mmol) was coupled with N-acetyl-1,3-ethyldiamine (133 mg, 1.30 mmol) then the product hydrogenated to give the title compound (176 mg, 0.42 mmol, 42%)

m.p. 167–169° C.

[α]$_D$=−4.2° (c=1, MeOH)

nu$_{max}$(KBr) 3280, 2930, 1640, 1540, and 700 cm$^{-1}$

δ$_H$ (250 MHz, D$_6$-DMSO) 0.72 (3H, d, J=6 Hz), 0.77 (3H, d, J=6 Hz), 1.30 (2H, t, J=10 Hz), 1.78 (3H, s), 2.06 (1H, m), 2.18 (1H, m), 2.87 (2H, m), 3.04 (2H, s), 3.13 (2H, q, J=6 Hz), 3.36 (1H, m), 7.21 (5H, m), 7.78 (1H, s), 7.98 (1H, s), 8.08 (1H, d, J=8 Hz) and 8.77 (1H, s).

δ$_C$ (62.9 MHz, D$_6$-DMSO) 174.8, 171.2, 169.4, 167.8, 138.3, 129.2, 128.1, 128.2, 54.2, 37.2, 35.8, 25.3, 23.4, 22.8 and 22.01.

Analysis calculated for C$_{21}$H$_{32}$N$_4$O$_5$.0.4H$_2$O Required C 58.97H 7.73N 13.10 Found C 59.07H 7.60N 12.90

EXAMPLE 5

[4-(N-Hydroxyamino)-2R-isobutylsuccinyl]-L-phenylalanine-N-(3-(2-pyrrolidone)propyl) amide.

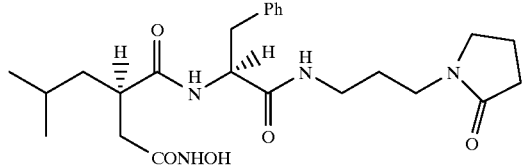

Using the procedure described in Example 1e [4-(N-Benzyloxyamino)-2R-isobutylsuccinyl]-L-phenylalanine (0.43 g, 1.0 mmol) was coupled with 1-(3-aminopropyl)-2-pyrrolidinone (180 mg, 1.26 mmol) then the product hydrogenated to give the title compound (280 mg, 0.61 mmol, 61%)

m.p. 174–176° C.

$[\alpha]_D$=−8.7° (c=1.35, MeOH)

$nu_{max}$(KBr) 3270, 3220, 2960, 1660, 1640, and 1525 cm$^{-1}$ $\delta_H$ (250 MHz, D$_6$-DMSO) 0.72 (3H, d, J=6 Hz), 0.77 (3H, d, J=6 Hz), 0.98 (1H, m), 1.33 (2H, m), 1.52 (2H, m), 1.87–2.06 (4H, m), 2.20 (2H, t, J=8 Hz), 2.62 (1H, m), 2.83 (1H, dd, J=14,9 Hz), 2.99 (1H, t, J=8 Hz), 3.10 (2H, t, J=7 Hz), 3.28 (2H, m), 4.39 (1H, m), 7.22 (5H, m), 7.91 (1H, m), 8.09 (1H, d, J=8 Hz), 8.80 (1H, bs), and 10.4 (1H,bs).

$\delta_C$ (62.9 MHz, D$_6$-DMSO) 174.0, 171.0, 167.7, 138.3, 129.2, 128.1, 126.2, 54.2, 46.6, 40.9, 40.6, 39.6, 38.7, 37.4, 36.5, 35.3, 30.6, 26.9, 25.3, 23.4, 22.1 and 17.7.

Analysis calculated for C$_{24}$H$_{36}$N$_4$O$_5$ Required C 62.59H 7.88N 12.16 Found C 62.67H 7.96N 12.22

EXAMPLE 6

[4-(N-Hydroxyamino)-2R-isobutylsuccinyl]-L-phenylalanine-N-(3-(2-pyrrolidone)propyl) amide sodium salt.

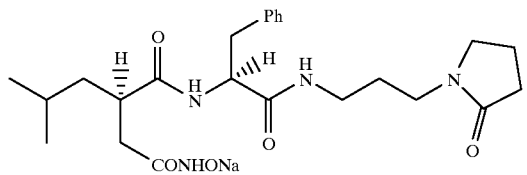

[4-(N-Hydroxyamino)-2R-isobutylsuccinyl]-L-phenylalanine-N-(3-(1-pyrrolidone)propyl) amide (50 mg, 0.109 mmol) was dissolved in methanol (20 ml) and sodium hydroxide solution (1.0M, 0.11 ml) added to give a homogeneous solution. The methanol was removed under reduced pressure then the residual aqueous solution freeze dried to give the title compound (52 mg, 0.108 mmol, 99%).

$\delta_H$ (250 MHz, D$_6$-DMSO) 0.66 (3H, d, J=6 Hz), 0.75 (3H, d, J=6 Hz), 0.94 (1H, m), 1.04 (2H, m), 1.56 (2H, m), 1.92 (3H, m), 2.08 (1H, dd, J=14,8 Hz), 2.14 (2H, t, J=8 Hz), 2.45 (1H, m), 2.83 (1H, dd, J=14,10 Hz), 3.03 (2H, d, J=6 Hz), 3.13 (4H, m), 3.23–3.48 (6H, m), 4.35 (1H, m), 7.20 (5H, m), 8.20 (1H, d, J=8 Hz), and 8.53 (1H, s).

EXAMPLE 7

[4-(N-Hydroxyamino)-2R-isobutylsuccinyl]-L-phenylalanine-N-(2-acetoxyethyl) amide.

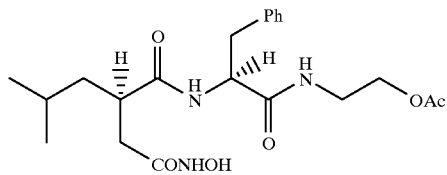

[4-(N-Hydroxyamino)-2R-isobutylsuccinyl]-L-phenylalanine-N-(2-hydroxyethyl)-amide (Example 1e, 148 mg, 0.32 mmol) was mixed with dimethylamino pyridine (40 mg, 0.33 mmol) in DCM at −30°, then acetic anhydride (32 mg, 0.32 mmol) was added and the reaction stirred for 25 min. The mixture was partitioned between ethyl acetate and water, the organic layer separated and washed sequentially with sodium bicarbonate, citric acid and brine then dried over sodium sulphate. Purification by column chromatography (ethyl acetate as eluant) gave protected material (130 mg) which was hydrogenated as before to give the title compound (62 mg, 0.15 mmol, 46%).

m.p. 136–137° C.

$[\alpha]_D$=−19.9° (c=1.2, MeOH)

$nu_{max}$(KBr) 3230, 2955, 1745, 1660, 1645, 1550 and 1235 cm$^{-1}$ $\delta_H$ (250 MHz, CDCl$_3$/D$_6$-DMSO) 0.71 (3H, d, J=6 Hz), 0.75 (3H, d, J=6 Hz), 0.99 (1H, m), 1.2–1.4 (2H, m), 1.96 (1H, m+3H, s), 2.11 (1H, dd, J=14,8 Hz), 2.59 (1H,m), 2.86 (1H, dd, J=14,9 Hz), 3.06 (1H, dd, J=14,5 Hz), 3.30 (2H, m), 3.95 (2H, t, J=6 Hz), 4.44 (1H, m), 7.16 (5H, m), and 8.00 (2H, m).

$\delta_C$ (62.9 MHz, D$_6$-DMSO) 174.1, 171.3, 170.1, 168.0, 138.0, 129.1, 127.9, 126.0, 78.8, 62.4, 41.0, 40.9, 37.8, 37.3, 35.8, 25.3, 23.1, 21.9 and 20.7.

Analysis calculated for C$_{21}$H$_{31}$N$_3$O$_6$.0.4H$_2$O Required C 58.84H 7.48N 9.80 Found C 58.91H 7.33N 9.55

EXAMPLE 8

[4-(N-Hydroxyamino)-2R-isobutyl-3S-methylsuccinyl]-L-phenylalanine-N-(3-(2-pyrrolidone)propyl) amide.

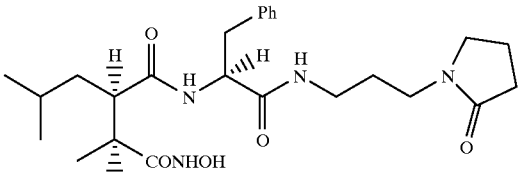

(a) 2S-tert-Butyl(3,3-di(benzyloxycarbonyl)-2,5-dimethyl) hexanoate

Benzyl (2-benzyloxycarbonyl-5-methyl) pentanoate (100 g, 0.29 mol) was dissolved in dry DMF (150 ml) and cooled while potassium tert-butoxide (31.1 g, 0.28 mol) was added portionwise over 10 minutes. This was then stirred for a further 1 hour until the solid had dissolved. To the resultant mixture, cooled to −20 to −30°, was added tert-butyl 2S-bromopropionate (60.6 g, 0.29 mol) in dry DMF (50 ml) over about 30 minutes. The reaction mixture was left at −20° for 3 days then 5° for 1 day before working up by partitioning between ether and ammonium chloride solution. The aqueous layer was extracted three times with ether then the combined organic layers washed with brine and dried. Solvent removal gave the crude title compound (141.2 g, 0.30 mol, 100%)

$[\alpha]_D$=33.0° (c=1.00, MeOH)

$\delta_H$(250 MHz, CDCl$_3$) 0.82 (6H, d, J=6 Hz), 1.28 (3H, t, J=7 Hz), 1.40 (9H, s), 1.46 (2H, m), 1.76 (1H, m), 1.92 (1H, dd, J=6,2 Hz), 5.11 (4H, m), and 7.27 (10H, m)

$\delta_C$ (62.9 MHz, CDCl$_3$) 172.7, 170.3, 135.3, 128.2, 80.8, 66.9, 58.7, 45.2, 42.5, 27.8, 24.4, 23.9, 23.8, and 14.3.

(b) 2S,3R tert-Butyl (3-carboxylic acid-2,5-dimethyl)-hexanoate

The crude material from Example 13a (141.2 g, 0.30 mol) was taken up n ethanol (200 ml) and refluxed with activated charcoal (10 g) for 1 hour to remove catalyst poisons. Cyclohexene (100 ml) and 10% palladium on charcoal (14 g) was added and the mixture refluxed for 2 hours. The catalyst was removed by filtration through celite and the solvent removed under reduced pressure.

The residual oil was taken up in xylene (200 ml) and refluxed for 30 minutes to effect decarboxylation. The solution was extracted with sodium carbonate solution (3×300 ml) this aqueous solution washed with ether then acidified to pH 5 with citric acid. The acidic solution was extracted with ethyl acetate (3×200 ml) then dried over sodium sulphate. Solvent removal then gave the crude title compound (53.2 g, 0.22 mol, 73%)

$[\alpha]_D$=8.0° (c=1.00, MeOH)

$\delta_H$(250 MHz, CDCl$_3$) 0.76 (6H, 2×d, J=6 Hz), 1.02 (3H, m), 1.28 (9H, s), 1.46 (2H, m), 2.42 (1H, m), and 2.58 (1H, m)

$\delta_C$ (62.9 MHz, CDCl$_3$) 173.9, 128.7, 46.5, 43.0, 39.1, 27.3, 26.2, 23.5, 21.4, and 14.9.

(c) [4-(tert-Butyloxy)-2R-isobutyl-3S-methylsuccinyl]-L-phenylalanine methyl ester The crude acid from Example 13b (45.0 g, 0.18 mol) was dissolved in DCM, then HOBT (24.9 g, 0.18 mol) added. The solution was cooled and NMM (18 g, 0.18 mol), phenylalanine methyl ester hydrochloride (36.1 g, 0.17 mol) and DCC (38 g, 0.18 mol) were added. This solution was stirred overnight, concentrated under vacuum then the precipitated DCU filtered off. The oily residue was dissolved in ethyl acetate then washed with 10% citric acid (2×250 ml), with 10% sodium bicarbonate (2×250 ml) and once with saturated brine (250 ml). The organic layer was dried (sodium sulphate), filtered then the solvent removed under reduced pressure to give the crude title compound as an oil (80.6 g, 0.20 mol, 120%).

(d) [4-(N-Benzyloxyamino)-2R-isobutyl-3S-methylsuccinyl]-L-phenylalanine methyl ester The crude tert-butyl ester (80.6 g, 0.20 mol) was dissolved in trifluroacetic acid/water (95:5, 85 ml) and left at 4° C. overnight. The solution was taken up in DCM, the aqueous layer re-extracted with DCM then the combined organic layers extracted with sodium bicarbonate (5×50 ml). The basic layer was acidified to pH 4 with citric acid then extracted with ethyl acetate. Drying and solvent removal gave the related acid (40.4 g, 0.115 mol. 69%).

The crude acid (40.4 g, 115 mmol) was dissolved in DCM/DMF (4:1, 500 ml), then HOBT (17.18 g 127 mol) and DCC (26.1 g, 127 mmol) were added and the mixture stirred at room temperature until tlc indicated complete conversion to the activated ester (about 10 minutes). To this solution containing the active ester was added benzylhydroxylamine (15.6 g, 127 mmol). After stirring at room temperature overnight DCM was removed under vacuum, the residue taken up in ethyl acetate then precipitated DCU removed by filtration. The solution was washed with citric acid (2×250 ml), 10% sodium bicarbonate solution (2×250 ml) and brine (250 ml) then finally dried over sodium sulphate. The solvent was removed under reduced pressure to give an oil (45.6 g) which was purified by recrystallisation from ethanol and DIPE (7.66 g, 17 mmol, 15%).

$\delta_H$ (250 MHz, CDCl$_3$) 0.47 (3H, d, J=7 Hz), 0.74 (3H, d, J=6 Hz), 0.83 (3H, d, J=6 Hz), 1.35 (2H, m), 1.94 (1H, dd, J=7,11 Hz), 2.38 (1H, m), 2.83 (1H, dd, J=14,11 Hz), 3.06 (1H, dd, J=5,14 Hz), 3.29 (3H, s), 3.62 (3H, s), 4.58 (1H, m), 4.77 (2H, s), 7.20 (5H, m), 7.38 (5H, s), and 8.49 (1H, d, J=8 Hz).

(e) [4-(N-Benzyloxyamino)-2R-isobutyl-3S-methyl-succinyl]-L-phenylalanine

[4-(N-Benzyloxyamino)-2R-isobutyl-3S-methyl-succinyl]-L-phenylalanine methyl ester (7.66 g, 17 mmol) was dissolved in methanol (120 ml) and sodium hydroxide solution (1.0M, 20.3 ml, 20.3 mmol) was added with stirring at room temperature. When the reaction was complete, as judged from tlc, the methanol was removed by evaporation the residue extracted with ether to remove starting material (2.1 g, 4.6 mmol, 21% recovered). The aqueous phase was acidified to pH4 with citric acid and extracted with ethyl acetate to give the title compound (5.88 g, 13.3 mmol, 79%).

$\delta_H$ (250 MHz, CDCl$_3$) 0.47 (3H, d, J=7 Hz), 0.74 (3H, d, J=6 Hz), 0.83 (3H, d, J=6 Hz), 1.35 (2H, m), 1.94 (1H, dd, J=7,11 Hz), 2.38 (1H, m), 2.83 (1H, dd, J=14,11 Hz), 3.06 (1H, dd, J=5,14 Hz), 3.29 (3H, s), 3.62 (3H, s), 4.58 (1H, m), 4.77 (2H, S), 7.20 (5H, m), 7.38 (5H, s), and 8.49 (1H, d, J=8 Hz).

(f) [4-(N-Hydroxyamino)-2R-isobutyl-3S-methyl-succinyl]-L-phenylalanine-N-(3-(2-pyrrolidone)propyl) amide.

[4-(N-Benzyloxyamino)-2R-isobutyl-3S-methylsuccinyl]-L-phenyl alanine (400 mg, 0.9 mmol), HOBT (134 mg, 1.0 mmol) and NMM (102 mg, 1,0 mmol) were dissolved in DCM/DMF (4:1, 10 ml) and cooled in ice. 1-(3-Aminopropyl)-2-pyrrolidinone (142 mg, 1.0 mmol) was added together with WSCDI (192 mg, 1.0 mmol). After 2 h at room temperature the reaction mixture was diluted with ethyl acetate then washed with sodium bicarbonate solution and brine, then dried over sodium sulphate. Solvent removal under reduced pressure gave the crude benzyl hydroxamate which was recrystallised from ethyl acetate/hexane (385 mg, 0.68 mmol)

The material from above was dissolved in cyclohexene/ethanol (10% solution, 20 ml), 10% palladium on charcoal (50 mg) was added then the mixture refluxed until starting material had dissappeared by tlc (ca. 30 minutes). The catalyst was removed by filtration, and the solvent removed under reduced pressure to leave a solid which could be recrystallised from ethyl acetate/ethanol. The required product (243 mg, 0.51 mmol, 76%) was collected by filtration.

m.p. 198–200° C.

$[\alpha]_D$=73.0° (c=1.00, MeOH)

nu$_{max}$(KBr) 3380, 2960, 1635, 1345, 1030, and 715 cm$^{-1}$ $\delta_H$(250 MHz, D$_6$-DMSO) 0.44 (3H, d, J=7 Hz, CHC$\underline{H}_3$), 0.72 (3H, d, J=6 Hz, CH(C$\underline{H}_3$)$_2$), 0.80 (3H, d, J=6 Hz, CH(C$\underline{H}_3$)$_2$), 1.32 (2H, m), 1.53 (2H, q, J=7 Hz), 1.92 (4H, m), 2.21 (2H, t, J=8 Hz), 2.37 (1H, m), 2.79 (1H, m), 2.93 (1H, d, J=5 Hz), 3.01 (2H, m), 3.13 (2H, t, J=7 Hz), 3.32 (6H, m), 4.54 (1H, m), 7.25 (5H, m), 7.80 (1H, t, J=7 Hz), 8.20 (1H, d, J=8 Hz, N$\underline{H}$), 8.69 (1H, s), and 10.36 (1H, s).

$\delta_C$ (62.9 MHz, D$_6$-DMSO) 174.0, 173.9, 171.4, 171.2, 138.2, 129.3, 128.0, 126.3, 54.6, 47.0, 46.7, 37.7, 36.3, 30.7, 27.3, 25.4, 24.3, 21.5, 17.7 and 16.1.

Analysis calculated for $C_{25}H_{38}N_4O_5 \cdot 0.5\,H_2O$ Required C 62.20 H 7.93 N 11.50 Found C 63.27 H 8.07 N 11.50

EXAMPLE 9

[4-(N-Hydroxyamino)-2R-isobutyl-3S-methylsuccinyl]-L-phenylalanine-N-methyl-N-(2-hydroxyethyl) amide.

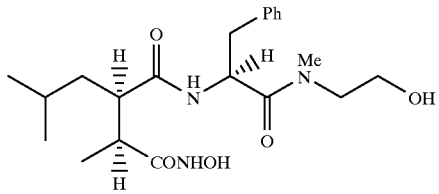

Using the procedure described in Example 13f [4-(N-Benzyloxyamino)-2R-isobutyl-3S-methylsuccinyl]-L-phenylalanine (0.4 g, 0.91 mmol) was coupled with N-methylethanolamine (75 mg, 1.00 mmol) then the product hydrogenated to give the title compound (100 mg, 0.25 mmol, 27%)

m.p. 182–183° C.

$[\alpha]_D = 27.0°$ (c=0.25, MeOH)

$\nu_{max}$(KBr) 3400, 3240, 2960, 1660, and 1545 cm$^{-1}$ $\delta_H$ (250 MHz, $D_6$-DMSO, mixture of rotamers) 0.46+ 0.54 (3H, d, J=6 Hz, CHC$\underline{H}_3$), 0.72+0.79 (6H, m, CH(C$\underline{H}_3$)$_2$), 1.3 (2H, m), 2.0 (1H, m), 2.4 (1H, m), 2.81+3.03 (3H, s, N(C$\underline{H}_3$)), 2.8–3.9 (8H, m), 5.0 (1H,m), 7.27 (5H, m), 8.35 (1H, d, J=8 Hz, N$\underline{H}$), and 8.73 (1H,m).

$\delta_C$ (62.9 MHz, $D_6$-DMSO, mixture of rotamers), 173.3, 173.2, 171.6, 171.4, 171.0, 138.3, 138.0, 129.4, 128.1, 128.0, 126.4, 126.3, 58.8, 58.5, 51.4, 50.2, 50.1, 49.9, 46.7, 40.1, 37.4, 37.1, 36.2, 33.9, 25.5, 25.4, 24.2, 24.1, 21.8, 21.7, 16.3, and 16.2.

Analysis calculated for $C_{21}H_{33}N_3O_5 \cdot H_2O$ Required C 59.28 H 8.29 N 9.87 Found C 59.30 H 7.91 N 9.94

EXAMPLE 10

[4-(N-Hydroxyamino)-2R-isobutyl-3S-methylsuccinyl]-L-phenylalanine-N-(2-hydroxyethyl) amide.

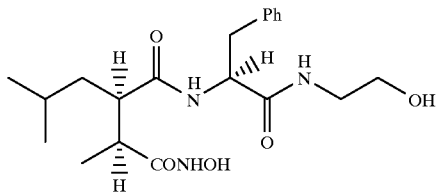

Using the procedure described in Example 13f [4-(N-Benzyloxyamino)-2R-isobutyl-3S-methylsuccinyl]-L-phenylalanine (0.4 g, 0.91 mmol) was coupled with ethanolamine (61 mg, 1.00 mmol) then the product hydrogenated to give the title compound (51 mg, 0.13 mmol, 14%)

m.p. 208–210° C.

$[\alpha]_D = 24.0°$ (c=0.30, MeOH)

$\nu_{max}$(KBr) 3280, 2960, 1635, 1540, 1450, and 1370 cm$^{-1}$ $\delta^H$ (250 MHz, $D_6$-DMSO) 0.39 (3H, d, J=6 Hz, CHC$\underline{H}_3$), 0.73 (3H, d, J=6 Hz, CH(C$\underline{H}_3$)$_2$), 0.80 (3H, d, J=6 Hz, CH(C$\underline{H}_3$)$_2$), 1.33 (2H, t, J=10 Hz), 1.94 (1H, t, J=8 Hz), 2.34 (1H, t, J=10 Hz), 2.77 (2H, t, J=12 Hz), 3.01 (2H, dd, J=11.3 Hz), 3.13 (2H, q, J=6 Hz), 4.61 (1H, m), 4.66 (1H,m), 7.20 (5H, m), 7.73 (1H, s), 8.18 (1H, d, J=8 Hz, N$\underline{H}$), and 8.69 (1H, s).

$\delta_C$ (62.9 MHz, $D_6$-DMSO) 173.5, 171.4, 138.3, 128.1, 126.3, 59.9, 54.2, 46.2, 41.6, 37.4, 25.4, 24.3, 21.7, and 16.1.

Analysis calculated for $C_{20}H_{31}N_3O_5 \cdot 0.5H_2O$ Required C 59.68 H 8.01 N 10.44 Found C 59.38 H 7.71 N 10.27

EXAMPLE 11

[4-(N-Hydroxyamino)-2R-isobutyl-3S-methylsuccinyl]-L-phenylalanine-N-(3-(2-pyrrolidone)propyl) amide sodium salt.

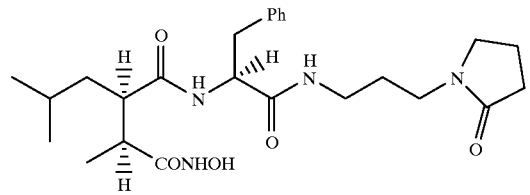

[4-(N-Hydroxyamino)-2R-isobutyl-3S-methylsuccinyl]-L-phenylalanine-N-(3-(1-pyrrolidone)propyl) amide (50 mg, 0.1 mmol) was dissolved in methanol (1 ml) and sodium hydroxide solution (1.0M, 2.0 ml) added to give a homogeneous solution. The methanol was removed under reduced pressure then the residual aqueous solution freeze dried to give the title compound (53 mg, 0.1 mmol, 100%).

$\delta_H$ (250 MHz, $D_6$-DMSO) 0.44 (3H, d, J=7 Hz, CHC$\underline{H}_3$), 0.72 (3H, d, J=6 Hz, CH(C$\underline{H}_3$)$_2$), 0.79 (3H, d, J=6 Hz, CH(C$\underline{H}_3$)$_2$), 1.32 (2H, m), 1.53 (2H, q, J=7 Hz), 1.92 (4H, m), 2.21 (2H, t, J=8 Hz), 2.37 (1H, m), 2.79 (1H, m), 2.93 (1H, d, J=5 Hz), 3.01 (2H, m), 3.13 (2H, t, J=7 Hz), 3.26–3.43 (6H, m), 4.54 (1H, m), 7.22 (5H, m), 7.85 (1H, J=7 Hz), and 8.28 (1H, d, J=8 Hz, N$\underline{H}$).

$\delta_C$ (62.9 MHz, $D_6$-DMSO) 174.0, 173.4, 170.8, 129.2, 127.7, 126.0, 54.6, 47.0, 46.7, 37.7, 36.3, 30.7, 27.3, 25.4, 24.3, 21.5, 17.7 and 16.1.

EXAMPLE 12

Collagenase inhibition activity

The potency of compounds of general formula I to act as inhibitors of collagenase (a metalloprotease involved in tissue degradation) was determined by the procedure of Cawston and Barrett, (*Anal. Biochem.*, 99, 340–345, 1979), hereby incorporated by reference, whereby a 1 mM solution of the inhibitor being tested or dilutions thereof was incubated at 37° for 16 hours with collagen and collagenase (buffered with 25 mM Hepes, pH 7.5 containing 5 mM CaCl$_2$, 0.05% Brij 35 and 0.02% NaN$_3$). The collagen was acetylated $^{14}$C collagen prepared by the method of Cawston and Murphy (*Methods in Enzymology*, 80, 711, 1981), hereby incorporated by reference. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported below as that inhibitor concentration effecting 50% inhibition of the collagenase ($IC_{50}$).

| Compound of Example No. | $IC_{50}$ |
|---|---|
| 2 | 200 nM |
| 3 | 20 nM |
| 4 | 90 nM |

Examples of unit dosage compositions are as follows:

EXAMPLE 13

Capsules:

| | Ingredients | Per Capsule | Per 10,000 Capsules |
|---|---|---|---|
| 1. | Active ingredient (Cpd of Formula I) | 40.0 mg | 400 g |
| 2. | Lactose | 150.0 mg | 1500 g |
| 3. | Magnesium stearate | 4.0 mg | 40 g |
| | | 194.0 mg | 1940 g |

Procedure for capsules

Step 1. Blend ingredients No. 1 and No. 2 in a suitable blender.

Step 2. Pass blend from Step 1 through a No. 30 mesh (0.59 mm) screen.

Step 3. Place screened blend from Step 2 in a suitable blender with ingredient No. 3 and blend until the mixture is lubricated.

Step 4. Fill into No. 1 hard gelatin capsule shells on a capsule machine.

EXAMPLE 14

Tablets:

| | Ingredients | Per Tablet | Per 10,000 Tablets |
|---|---|---|---|
| 1. | Active ingredient (Cpd of Form. I) | 40.0 mg | 400 g |
| 2. | Corn Starch | 20.0 mg | 200 g |
| 3. | Alginic acid | 20.0 mg | 200 g |
| 4. | Sodium alginate | 20.0 mg | 200 g |
| 5. | Magnesium stearate | 1.3 mg | 13 g |
| | | 101.3 mg | 1013 g |

Procedure for tablets

Step 1. Blend Ingredients No. 1, No. 2, No. 3 and No. 4 in a suitable mixer/blender.

Step 2. Add sufficient water portionwise to the blend from Step 1 with careful mixing after each addition. Such additions of water and mixing until the mass is of a consistency to permit its conversion to wet granules.

Step 3. The wet mass is converted to granules by passing it through an oscillating granulator using a No. 8 mesh (2.38 mm) screen.

Step 4. The wet granules are then dried in an oven at 140° F. (60° C.) until dry.

Step 5. The dry granules are lubricated with ingredient No. 5.

Step 6. The lubricated granules are compressed on a suitable tablet press.

EXAMPLE 15

Intramuscular Injection:

| | Ingredient | Per ml. | Per liter |
|---|---|---|---|
| 1. | Formula I compound Active ingredient | 10.0 mg | 10 g |
| 2. | Istonic buffer solution pH 4.0. | q.s. | q.s |

Procedure

Step 1. Dissolve the active ingredient in the buffer solution.

Step 2. Aseptically filter the solution from Step 1.

Step 3. The sterile solution is now aseptically filled into sterile ampoules.

Step 4. The ampoules are sealed under aspetic conditions.

EXAMPLE 16

Suppositories:

| | Ingredients | Per Supp. | Per 1,000 Supp |
|---|---|---|---|
| 1. | Formula I compound Active ingredient | 40.0 mg | 40 g |
| 2. | Polyethylene Glycol 1000 | 1350.0 mg | 1,350 g |
| 3. | Polyethylene Glycol 4000 | 450.0 mg | 450 g |
| | | 1840.0 mg | 1,840 g |

Procedure

Step 1. Melt ingredient No. 2 and No. 3 together and stir until uniform.

Step 2. Dissolve ingredient No. 1 in the molten mass from Step 1 and stir until uniform.

Step 3. Pour the molten mass from Step 2 into suppository moulds and chill.

Step 4. Remove the suppositories from moulds and wrap.

EXAMPLE 17

Eye Ointment

An appropriate amount of a compound of general formula I is formulated into an eye ointment base having the following composition:

| Liquid paraffin | 10% |
|---|---|
| Wool fat | 10% |
| Yellow soft paraffin | 80% |

EXAMPLE 18

Topical skin ointment

An appropriate amount of a compound of general formula I is formulated into a topical skin ointment base having the following composition:

| | |
|---|---|
| Emulsifying wax | 30% |
| White soft paraffin | 50% |
| Liquid paraffin | 20% |

We claim:

1. A compound of formula I:

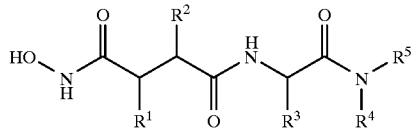

(I)

wherein

R$^1$ represents a hydrogen atom or a C$_1$–C$_6$ alkyl, C$_1$–C$_6$ alkenyl, phenyl, phenyl (C$_1$–C$_6$)alkyl, C$_1$–C$_6$ alkythiomethyl, phenylthiomethyl, substituted phenylthiomethyl, phenyl(C$_1$–C$_6$)alkythiomethyl, pyridine-2-thiomethyl, pyridine-4-thiomethyl, thiophene-2-thiomethyl or pyrimidine-2-thiomethyl group wherein substituted refers to up to four substituents each of which independently may be C$_1$–C$_6$ alkyl, C$_1$–C$_6$ alkoxy, hydroxy, thiol, C$_1$–C$_6$ alkylthiol, amino, halo, triflouromethyl, nitro, —COOH, —COONH$_2$ or —CONHR$^A$, wherein R$^A$ represents a C$_1$–C$_6$ alkyl group or the side chain of the amino acid alanine, valine, leucine, isoleucine, phenylalanine, tryptophan, methionine, glycine, serine, threonine, cysteine, tyrosine, asparagine, glutamine, aspartic acid, glutamic acid, lysine, arginine or histidine; or R$^1$ represents —S—R$^x$ wherein R$^x$ represents a group;

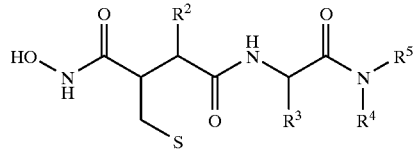

R$^2$ represents a hydrogen atom or a C$_1$–C$_6$ alkyl, C$_1$–C$_6$ alkenyl, phenyl (C$_1$–C$_6$) alkyl, cycloalkyl (C$_1$–C$_6$) alkyl, or cycloalkenyl (C$_1$–C$_6$) alkyl;

R$^3$ represents an amino acid side chain or a C$_1$–C$_6$ alkyl, benzyl, (C$_1$–C$_6$) alkoxylbenzyl, benzyloxy (C$_1$–C$_6$) alkyl or benzyloxybenzyl group;

R$^4$ represents a hydrogen atom or a methyl group;

R$^5$ represents a group (CH$_2$)$_n$A;

n is an integer from 1 to 6;

A represents a hydroxy, (C$_2$–C$_7$)acyloxy, (C$_1$–C$_6$) alkylthio, phenylthio, or (C$_2$–C$_7$)acylamino;

or a pharmaceutically acceptable salt or N-oxide or where the compound is a thio-compound, a sulphoxide or sulphone thereof.

2. A compound as claimed in claim 1, in which the chiral centre adjacent the substituent R$^3$ has S stereochemistry.

3. A compound as claimed in claim 1, wherein R$^1$ represents a hydrogen atom or a C$_1$–C$_4$ alkyl, phenylthiomethyl or heterocyclythiomethyl group.

4. A compound as claimed in claim 1, wherein R$^2$ represents a C$_2$–C$_6$ alkyl group.

5. A compound as claimed in claim 1, wherein R$^3$ represents a benzyl, 4-(C$_1$–C$_6$) alkoxyphenylmethyl or benzyloxy benzyl group.

6. A compound as claimed in claim 1 wherein n has the value 1, 2 or 3.

7. A compound as claimed in any one of claims 1 to 6, wherein R$^5$ represents a pyrrolidone, hydroxy, methoxy or thioethyl group.

8. A compound selected from the group consisting of:

(4-(N-Hydroxyamino)-2R-isobutylsuccinyl)-L-phenylaianine-N-(2-hydroxyethyl)-amide;

(4-(N-Hydroxyamino)-2R-isobutylsuccinyl)-L-phenylalanine-N-(2-hydroxyethyl)-N-methylamide;

(4-(N-Hydroxyamino)-2R-isobutylsuccinyl)-L-phenylalanine-N-(2-ethyl thioethyl)-amide;

(4-(N-Hydroxyamino)-2R-isobutylsuccinyl)-L-phenylalanine-N-(2-N-acetylethyl)-2-aminoethyl amide;

(4-(N-Hydroxyamino)-2R-isobutylsuccinyl)-L-phenylalanine-N-(2-acetoxyethyl)-amide;

(4(N-Hydroxyamino)-2R-isobutyl-3S-methylsuccinyl)-L-phenylalanine-N-methyl-N-(2-hydroxyethyl)-amide;

(4-(N-Hydroxyamino)-2R-isobutyl-3S-methylsuccinyl)-L-phenylalanine-N-(2-hydroxyethyl)-amide;

and pharmaceutically acceptable salts thereof.

* * * * *